United States Patent
Mousavi et al.

(10) Patent No.: US 8,378,304 B2
(45) Date of Patent: Feb. 19, 2013

(54) CONTINUOUS REFERENCING FOR INCREASING MEASUREMENT PRECISION IN TIME-DOMAIN SPECTROSCOPY

(75) Inventors: Payam Mousavi, Coquitlam (CA); Steven Dodge, Burnaby (CA); Frank Martin Haran, North Vancouver (CA); Stephane Savard, Vancouver (CA); David Jez, Vancouver (CA); Stuart James Heath, Surrey (CA)

(73) Assignee: Honeywell ASCa Inc., Mississauga (CA)

( * ) Notice: Subject to any disclaimer, the term of this patent is extended or adjusted under 35 U.S.C. 154(b) by 323 days.

(21) Appl. No.: 12/862,733

(22) Filed: Aug. 24, 2010

(65) Prior Publication Data

US 2012/0049070 A1 Mar. 1, 2012

(51) Int. Cl.
G01J 5/02 (2006.01)

(52) U.S. Cl. .................................................. 250/341.1

(58) Field of Classification Search .................. 250/340, 250/341.1, 341.2, 341.4, 341.5, 341.8
See application file for complete search history.

(56) References Cited

U.S. PATENT DOCUMENTS

| 4,626,773 | A | 12/1986 | Kroeger |
| 5,491,552 | A | 2/1996 | Knüttel |
| 6,865,014 | B2 | 3/2005 | Ciesla |
| 7,184,810 | B2 | 2/2007 | Caduff |
| 2004/0065832 | A1 | 4/2004 | Cluff |
| 2005/0082479 | A1 | 4/2005 | Wallace |
| 2006/0045807 | A1* | 3/2006 | Zhang et al. ............... 422/82.05 |
| 2006/0063188 | A1 | 3/2006 | Zanni |
| 2008/0165355 | A1 | 7/2008 | Yasui |
| 2008/0239317 | A1 | 10/2008 | Schulkin |
| 2009/0152469 | A1 | 6/2009 | Nishizawa |
| 2010/0007955 | A1 | 1/2010 | Beselt |
| 2010/0024999 | A1 | 2/2010 | Haran |

OTHER PUBLICATIONS

PCT/CA2011/000938 Search Report dated Apr. 24, 2012.

* cited by examiner

*Primary Examiner* — Mark R Gaworecki
(74) *Attorney, Agent, or Firm* — Cascio Schmoyer & Zervas (57) ABSTRACT

An apparatus for incorporation into time-domain spectroscopy systems that creates a continuous reference whereby a sample pulses' phase and amplitude can be tracked and corrected employs a beam splitter to generate sample and reference pulses. A detector is positioned for receiving the reference radiation pulses that do not interact with the sample. The same detector is also positioned for receiving the sample radiation pulses that emerge from the sample. The apparatus can be readily implemented by being configured between the emitter and detector of a terahertz time-domain spectrometer. The reference pulse is used to trace the changes in time and amplitude of the sample pulse. Since any changes in the reference pulse will most likely manifest in the sample pulse, the reference pulse is monitored and used to correct the sample pulse and thereby reduce the effects of jitter.

17 Claims, 7 Drawing Sheets

CONTINUOUS REFERENCING FOR INCREASING MEASUREMENT PRECISION IN TIME-DOMAIN SPECTROSCOPY

FIELD OF THE INVENTION

The present invention generally relates to time-domain systems and methods and specifically to techniques for time-domain spectrometers that enable the sample pulses' phase and amplitude to be tracked and corrected by means of reference pulses thereby significantly increasing the measurement precision of time-domain spectrometers.

BACKGROUND OF THE INVENTION

Time-domain systems are important analytical tools for measuring properties of an object. Recently, terahertz systems known as terahertz time-domain spectrometers (THz-TDS) have been developed. These systems often use visible to near-infrared laser pulses each lasting only 10 to several hundred femtoseconds to electromagnetic pulses ("T-rays") that each last for about a picosecond. T-rays can be transmitted through various objects, using an imaging system of lenses and mirrors to focus or collimate the T-rays. As the T-rays pass through the object under test, they are typically distorted. These changes in the T-ray signals can be analyzed to determine properties of the object. Materials can be characterized by measuring the amounts of distortion-from absorption, dispersion and reflection-of the T-rays passing through to a detector. A digital signal processing system takes the digitized data from the THz detector and analyzes the data in either the spectral or temporal domain.

Because many compounds change T-rays in characteristic ways (e.g., absorption or dispersion), molecules and chemical compounds show strong absorption lines that can serve as "fingerprints" of the molecules. T-ray spectroscopy can distinguish between different chemical compositions inside a material even when the object looks uniform in visible light. A terahertz sensor for instance can be employed to measure caliper, moisture, and basis weight of paper whose thickness is similar to the wavelengths of T-Rays.

The precision of amplitude and phase measurements in time-domain (terahertz) spectroscopy (THz-TDS) is often limited by noise in the system. It has been demonstrated that the dominant types of noise present in THz-TDS are often time base and amplitude jitter characterized by pulses traveling through the same material (or air) which reach the detector at slightly different times and with slightly different amplitudes due to fluctuations in environmental parameters (e.g., temperature fluctuations or vibrations) or hardware errors (e.g., encoder errors in the delay line). In some specific THz-TDS systems, jitter makes a significant contribution to the noise and therefore limits the measurement precision of the system. In other THz-TDS systems, it is the multiplicative noise (i.e., amplitude noise), which comes primarily from the laser that is the main source of imprecision.

Prior art endeavors to reduce the adverse effects of jitter focused on controlling environmental parameters such as temperature and minimizing vibrations. In addition, improving the quality of the delay stage was also an important consideration. For example, US Patent Application Publication 2010/0007955 to Beselt describes a large amplitude high frequency optical delay that is particularly suited for use in a scanning terahertz sensor system that employs optical fibers that serve as launching and returning optics.

SUMMARY OF THE INVENTION

The present invention is based in part on the development of an apparatus for implementation of time-domain spectroscopy that creates a continuous set of reference pulses whereby a sample pulses' phase and amplitude can be tracked and corrected. The apparatus can be readily adopted in any existing time-domain spectrometer where both amplitude and phase are of interest. A feature of the apparatus is that when it is employed in a THz-TDS, the effect of jitter can be significantly reduced. Also when the inventive technique used in conjunction with THz-TDS, the emitter does not have to move off the sample to collect reference pulses required to do further analysis. This could potentially simplify the design of the final sensor.

In one aspect, the invention is directed to an apparatus that has a continuous reference for measuring at least one property of a sample that includes:
  a radiation source that generates pulses of radiation;
  means for splitting the pulses of radiation to yield reference radiation pulses and sample radiation pulses wherein the sample radiation pulses are directed to the sample; and
  a detector positioned for receiving the reference radiation pulses wherein the reference radiation pulses do not interact with the sample, and wherein the detector is positioned for receiving the sample radiation pulses that emerge (transmitted or reflected) from the sample.

In another aspect, the invention is directed to a time-domain spectroscopy apparatus that has a continuous reference for measuring at least one property of a sample that includes:
  an emitter that generates pulses of radiation;
  means for splitting the pulses of radiation to yield reference radiation pulses and sample radiation pulses wherein the sample radiation is directed to the sample and wherein the reference radiation pulses do not interact with the sample;
  a first mirror positioned to reflect sample radiation that has been transmitted through or reflected from the sample;
  a second mirror positioned to reflect the reference radiation pulses; and
  a detector positioned for receiving the reflected reference radiation pulses and the reflected sample radiation pulses.

In yet another aspect, the invention is directed to a method of improving the precision of a time-domain spectroscopy apparatus that includes an emitter that generates pulses of radiation and a detector that receives pulses of radiation that emerge from a sample, the method including the steps of:
  positioning a beam splitter along an optical path between the emitter and the detector to form reference radiation pulses and sample radiation pulses that are directed to the sample and the reference radiation pulses do not interact with the sample;
  positioning a first mirror to reflect sample radiation pulses to the detector; and
  positioning a second mirror to reflect reference radiation pulses to the detector and using the reflected radiation pulses to monitor fluctuations in phase and amplitude of the reference radiation pulses.

DESCRIPTION OF PREFERRED EMBODIMENTS

The present invention is directed to techniques for enhancing the precision of time-domain spectroscopy systems, which can be implemented by modifying standard time-domain spectrometers. While the invention will be described in relationship with a terahertz time-domain spectrometer, it is understood that the invention improves the precision of any time-domain spectrometer wherein pulses of radiation are applied to a sample and the time resolved characteristics of the reflected or transmitted pulses that emerge from the sample are analyzed. Further while the terahertz time-domain spectroscopy apparatus is described in the transmission mode, it is understood that the invention is also applicable in the reflection mode.

Figure 1:
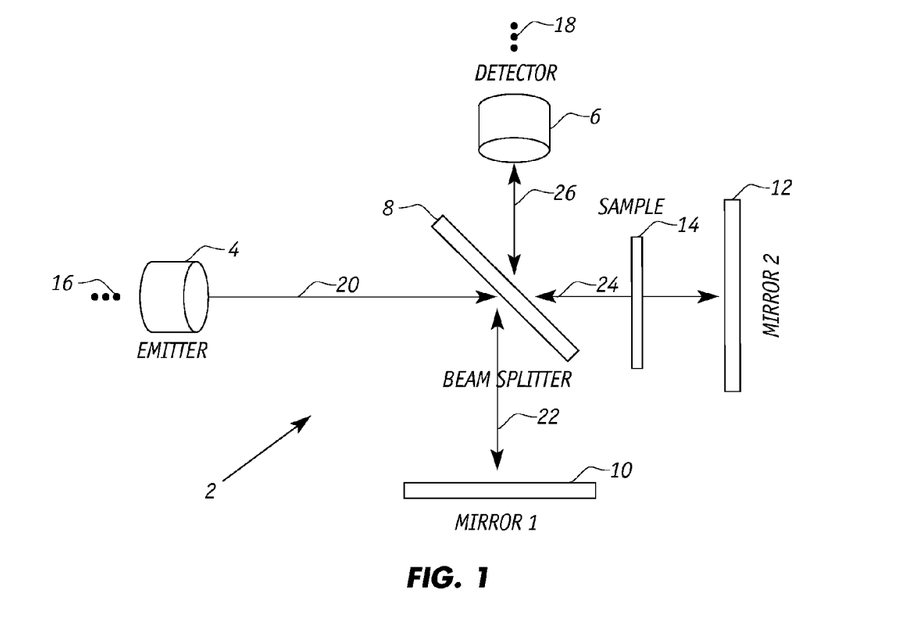
FIG. 1 depicts a device for generating continuous referencing in time-domain spectroscopy.

FIG. 1 illustrates one embodiment of the inventive continuous real time referencing generating device 2 that is positioned between an emitter 4 and a detector 6 of a standard time-domain spectrometer. A beam splitter 8 splits incident light 20 from emitter 4 into reflected light 22 and transmitted light 24. The reflected light 22 is reflected back by flat mirror 10 through beam splitter 8 before being received by detector 6. Similarly, transmitted light 24 is transmitted through sample 14 and thereafter reflected by flat mirror 12 back toward beam splitter 8 where it is reflected into detector 6. In the case where device 2 augments a terahertz spectrometer, the emitter and detector can be, for example, photoconductive antennae. For terahertz radiation, a preferred beam splitter comprises a thick piece of high resistivity (>10,000 O-cm) silicon slab. The thickness of the beam splitter is selected to be large enough so that reflections from the back surface thereof lie outside the measurement window. If a thinner beam splitter is used, the pulse shape will look different since multiple reflections from the back side are included in the window. In principal either configuration can be employed with the present invention. A thicker beam splitter is preferred because it is less prone to vibrate. The high resistivity silicon slab is particularly suited for use as a beam splitter as it has a high refractive index with acceptable absorption in terahertz frequencies. Alternatively, sapphire or polyethylene could be used as the beam splitter although they have higher absorption than that of silicon.

In operation, laser pulses 16 and 18 are directed to emitter and detector 18, respectively. Initially, a terahertz radiation pulse is generated by the photoconductive antenna emitter 4 and is incident on silicon beam splitter 8 at a 45 degrees angle resulting in two pulses traveling in perpendicular directions. One pulse is transmitted through sample 14 whereas the other pulse is used to track the fluctuations in time and amplitude. Since the two pulses are generated at the same time and position, their phases and amplitudes correlate very strongly and this correlation is used to correct measurement errors. This method is particularly suited for fiber optic based time domain terahertz spectrometers where the bending of fibers and temperature fluctuations could have strong adverse effects in precision in amplitude and phase measurements. A feature of the invention is that only one detector 6 is required. The use of single detector avoids introducing a set of variable attendant to a second detector.

Figure 2:
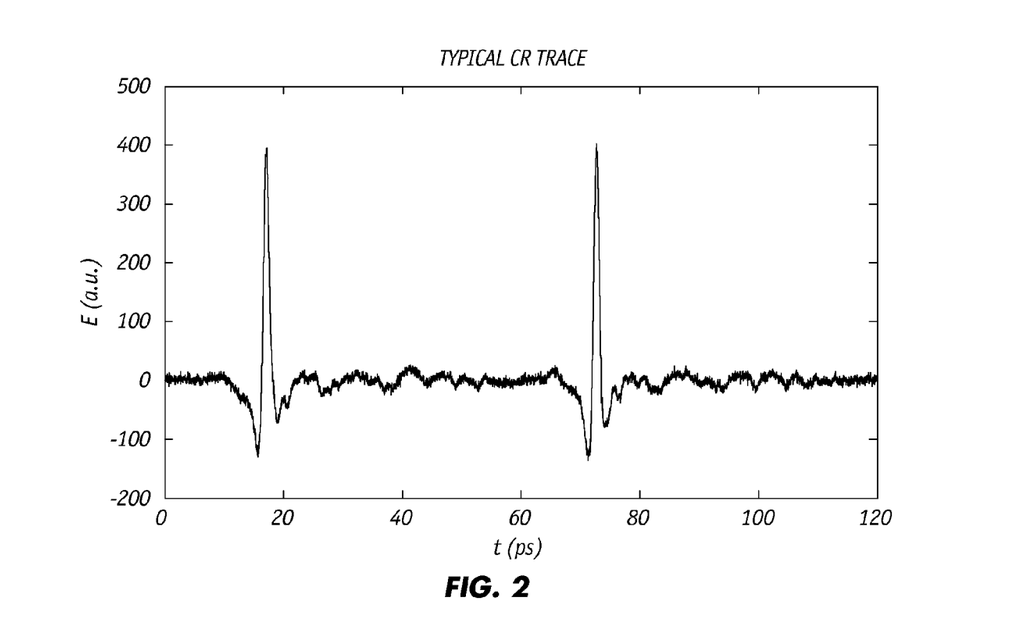
FIG. 2 shows a representative continuous referencing (CR) trace generated by a beam splitter.
Figure 5:
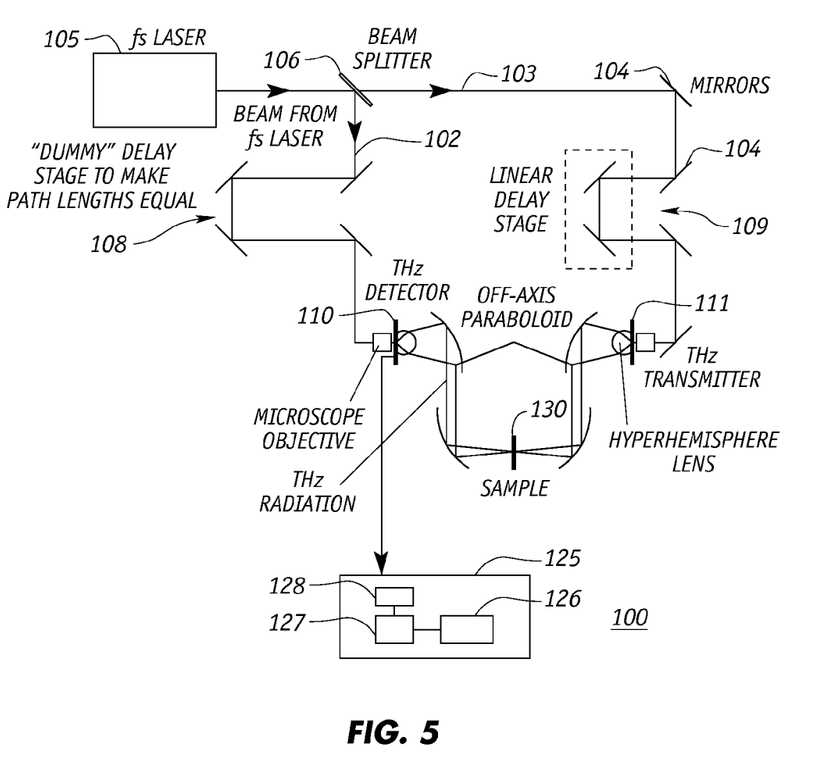
FIG. 5 is a representation of an exemplary THz or near THz-TDS transmission-based sheet measurement system.

The continuous real time referencing generating device of FIG. 1 was incorporated into a THz-TDS transmission-based sheet measurement system as shown in FIG. 5 and further described herein. By so modifying the system, for each pulse that is generated by the emitter of the terahertz spectrometer, the beam splitter generates two pulses one that passes through the sample of interest and the other pulse traveling through air. FIG. 2 depicts two representative pulses that are formed by the beam splitter. Each pulse has a characteristic profile and peak and, the left pulse is designated the "left" pulse and the right one the "right" pulse. An arbitrary point somewhere in the middle to separate the two can be selected. In the following analysis, the "right" pulse is used both as a reference (i.e., where the pulse travels through air) and as a sample pulse (i.e., where the pulse travels through a sample). These are two separate measurements conducted one after the other.

One method of implementing the continuous referencing procedure is to initially collect a set of reference pulses. In this set, the two pulses ("left" and "right") travel through air. Thereafter, a sample of interest is inserted in one of the arms of the spectrometer (i.e., the right arm) and a new data set is collected. All analysis can now be performed using the reference and sample "right" pulse measurements. The left pulse is used to trace the changes in time and amplitude of the right pulse. Since any changes in the "left" pulse will most likely manifest in the "right" pulse, the "left" pulse could be monitored and used to correct the "right" pulse and thereby reduce the effects of jitter.

Figure 3:
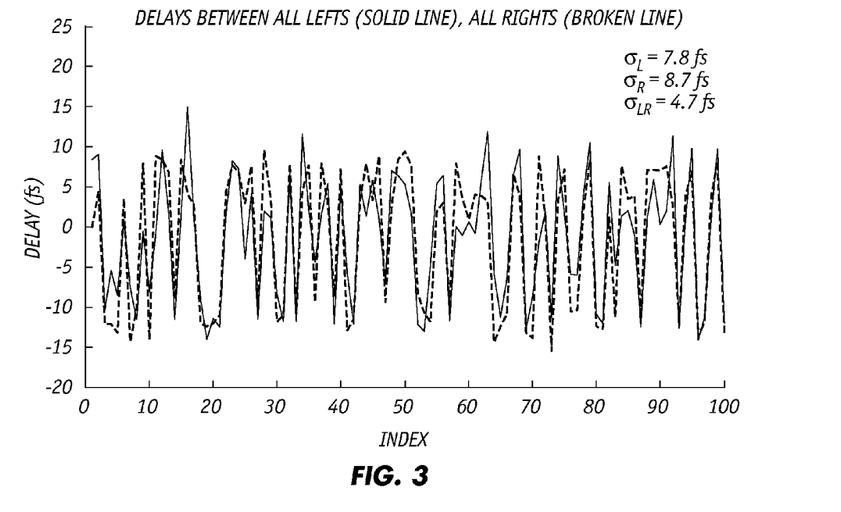
FIG. 3 compares the inter-pulse jitter between to sets of pulses.

FIG. 3 shows the inter-pulse time jitter between the "left" and "right" pulses for 100 different measured pulses. The "index" designation on the x-axis refers to the experiment measurement number (1-100) so that each point on the graph corresponds to a set of left and right pulses. The plot shows the pair wise time delay between the left and right pulses. This correlation plot further establishes that the two pulses move synchronously which permits the correction of time jitter in one of the pulses. The comparison demonstrates that the standard deviation of jitter could be reduced by a factor of 2.

Figure 4:
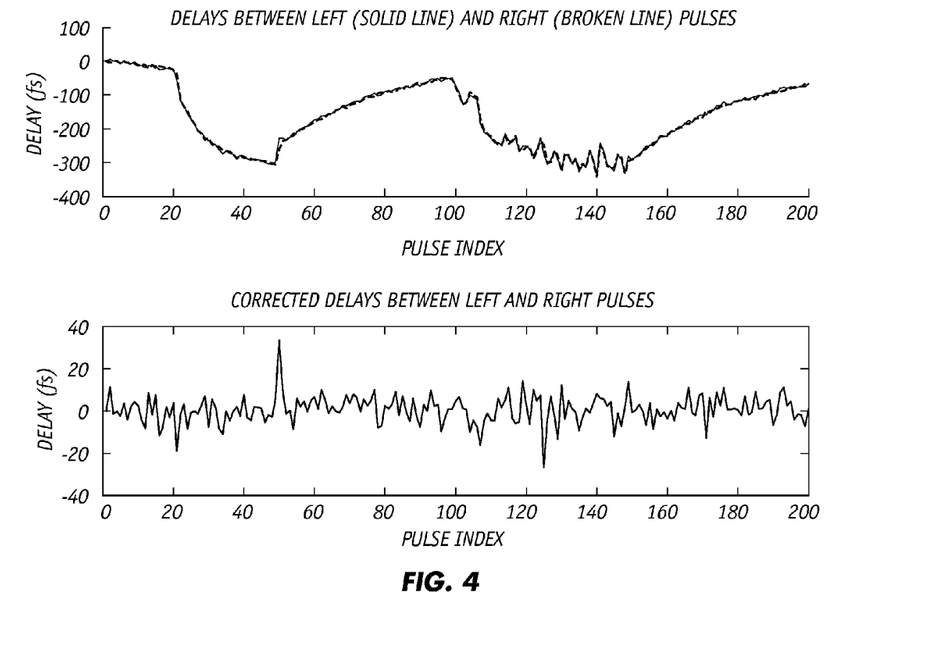
FIG. 4 are graphs that show the delays between two sets of pulses and corrected delays thereto.

For fiber optics based terahertz time-domain spectrometers where precise phase measurements are particularly critical, the inventive technique can compensate for the adverse effects of temperature and other factors that otherwise would interfere with phase measurements. In particular, for a fiber optics based spectrometer, a polarization and/or path length change occurs as a result of fibers being twisted or stretched that occurs with movement of the sensors as they scan the sample. The top plot of FIG. 4 is the inter-pulse time jitter between the "left" and "right" pulses for 200 different measured pulses as the fiber connections of the terahertz time-domain spectrometer were manually twisted to simulate the effects of movement for a scanning type system typically used in a paper machine. The plot shows that, the polarization change affects the delay of the pulses. The lower plot of FIG. 4 demonstrates that the inventive technique can be employed to track and correct these delays as the two pulses are affected similarly and one could be used to track the changes in the other.

Once the continuous set of reference pulses is obtained, the sample pulses' phase and amplitude can be tracked and corrected, as necessary. For example, time jitter can be corrected using the reference pulses by adding or subtracting a delay to the sample pulse. To correct for amplitude variations with the reference pulses, scaling of the sample amplitude by multiplicative factor can be used to increase or decrease its intensity.

The present invention can be implemented in time-domain spectroscopy systems. It has been demonstrated that near THz or THz-TDS can be used in-situ to coincidentally obtain one or more parameters/properties of a sheet material including the water weight, physical thickness (caliper) and dry weight volume fraction. The sheet material can comprise paper or a plastic. From these parameters/properties in combination with one or more calibration parameters, caliper, basis weight and moisture content including PM and/or WW of the sheet material may be obtained.

The calibration parameters generally include the known Debye parameters used in a double Debye model which obtains the dielectric constant of water in the THz or near THz spectral region of the electromagnetic spectrum, the dry content refractive index of the paper or other sheet material under test, the density of the dry content of the paper under test, and the coefficients of a fit of water weight to a log of the power ratio of reference signal to that of a transmitted (or reflected) sample signal.

Moisture content (such as expressed as percent moisture (PM)) and WW can be obtained by measuring the near THz or THz power or field transmitted through a sample and comparing it with a reference pulse (without sample) and therefore obtaining how much the water has attenuated the pulse. As known in the art, PM is related to WW via the relation: PM=WW/BW; where BW represents basis weight (repeated in equation 12 below). BW=WW+DW; where DW represents dry weight (no water present). From this attenuation measurement and calibration data (e.g. from a laboratory calibration), measurements relating to the amount of water present in the sheet material may be determined.

Moisture content (such as expressed as PM or WW) can also be obtained via a similar method in a system having reflection geometry. In a reflection-based system, the THz transmitter/emitter and THz receiver/detector on the same side of the sample. In such a system, the reference signal is taken from a non-water containing reflective surface and the sample signal is the reflected THz or near THz signal from the sample.

For transmittance-based systems: The sample caliper and dry weight volume fraction can be obtained by fitting a model for the transmittance function for a single layer film (e.g. sheet of paper) to that of the experimentally obtained transmitted THz pulse. One physical model that can be used is the following: [see Born, M. and Wolf, E, Principles of Optics, 4$^{th}$ edition, Pergamon Press (1970)]

$$t = \frac{t_{12} \cdot t_{23} \cdot e^{i\beta}}{1 + r_{12} \cdot r_{23} \cdot e^{2i\beta}} \quad (1)$$

Where $t_{12}$ and $t_{23}$ are the transmission coefficients at the first and second film layer interfaces respectively, $r_{12}$ and $r_{23}$ are the reflection coefficients at the first and second film layer interfaces respectively, and $\beta=\omega/c \cdot n_p \cdot h$. Where $\omega$ is the angular frequency of the THz radiation, c is the speed of light, h is the film thickness and $n_p$ is the complex refractive index of the film (e.g. paper). The transmission and reflection coefficients in equation (1) are given by:

$$t_{12} = \frac{2n_a}{n_a + n_p} \quad (2)$$

$$t_{23} = \frac{2n_p}{n_a + n_p}$$

$$r_{12} = \frac{n_a - n_p}{n_a + n_p}$$

$$r_{23} = \frac{n_p - n_a}{n_a + n_p}$$

Where $n_a$ and $n_p$ are the refractive indices of air and paper (or other sheet material), respectively. The refractive index of air is approximately equal to 1 and the refractive index of paper is determined by using an effective medium theory such as the classical Bruggeman model. The dry content refractive index is generally obtained via a calibration step and has been found by the authors to depend upon paper type. The refractive index of water is obtained via its dielectric function that can generally be accurately described with a double Debye model of the form:

$$\varepsilon_w(\omega) = \varepsilon_\infty + \frac{\varepsilon_s - \varepsilon_2}{1 + i\omega\tau_1} + \frac{\varepsilon_2 - \varepsilon_\infty}{1 + i\omega\tau_2} \quad (3)$$

Where $\in_s$ is the static dielectric constant, ex is the limiting value dielectric constant at high frequency, $\in_2$ is an intermediate value of dielectric constant and the time constant $\tau_1$ and $\tau_2$ are related to the translational and rotational diffusion, hydrogen bond rearrangement and structural rearrangement. Although a double Debye model is generally described herein to describe the water's dielectric constant, other models can also be used, e.g. single Debye model, or certain non-Debye-based models.

The refractive index of the sheet material can be obtained via the dielectric constant of the sheet material (e.g. paper) using the Bruggeman model:

$$\varepsilon_p(\omega) = \frac{1}{4}\left(\beta + \sqrt{\beta^2 + 8\varepsilon_d\varepsilon_\omega}\right) \quad (4)$$

$$\beta = (3f_d - 1)\varepsilon_d + (3f_w - 1)\varepsilon_w \quad (5)$$

Where $f_w$ and $f_d$ are the volume fractions of water and dry sheet material, such as paper. If the paper only contains water and dry content (e.g. cellulose) then $f_w=1-f_d$. It has been found by the present Inventors that $\in_d$ can be approximated as a real constant over the frequency range of interest. However, time-domain spectroscopy systems can include the case where the dielectric constant of the film could be absorptive (non-zero imaginary component to dielectric constant) and dispersive.

The refractive index is related to the dielectric function by the following expressions:

$$n_{real} = Re(\sqrt{\epsilon_p})$$

$$n_{img} = Im(\sqrt{\epsilon_p}) \quad (6)$$

In one embodiment, the transmittance of the THz pulse through the paper is modeled using the transmittance function given in equation (1). A two parameter least squares fit of the model to the experimentally obtained transmitted THz pulse can then be performed. The two fitted parameters obtained from the fit are dry content volume fraction and physical thickness. As described above the water content can be obtained from the amplitude of the transmitted pulse.

For reflection-based systems: The same methodology described above in the case of transmittance system arrangement can be used in a reflection arrangement where instead of the expression for transmission (equation (1)), an expression for the reflectance can be used:

$$r = \frac{r_{12} + r_{23} \cdot e^{2i\beta}}{1 + r_{12} \cdot r_{23} \cdot e^{2i\beta}} \quad (7)$$

FIG. 5 is a simplified representation of an exemplary THz or near THz-TDS transmission-based sheet measurement system 100, according to an embodiment of the invention. It has been demonstrated that with the THz-TDS system shown in FIG. 5, jitter limits the measurement precision of the system. It is expected that implementation of the constant referencing technique of the present invention will significantly enhance its precision. A variety of other THz-TDS-based measurement system arrangements may be used, since embodiments of the invention generally involve new uses for THz or near THz-TDS systems supported by new algorithms and related calibration data that permit in-situ coincident measurement of a plurality of properties of the sheet material including the moisture content (such as PM and/or WW), caliper (thickness) and basis weight.

System 100 comprises a near THz or THz generator including at least one pulsed laser source (e.g. femtosecond (fs) laser) 105 for emitting a beam of optical pulses. A beam splitter 106 splits the optical beam into two beams, a reflected beam 102 and a transmitted beam 103. The reflected beam 102 is directed to reflective delay comprising optics 108 including a "dummy" delay stage. The purpose of the dummy delay is to make both the source (transmitter) and receiver (detector) arms of the THz-TDS system 100 have nominally equal optical path lengths; this results in the source and receiver fs-pulses being derived from the same original fs-pulse. The intention of the dummy delay is to minimize noise. However this dummy delay is not generally required and the THz-TDS system 100 can be also generally operated without it in certain applications.

The transmitted beam 103 is directed via mirrors 104 to delay comprising optics 109 shown as linear delay stage. The delay comprising optics 108 and 109 are configured to make the optical path length of the reflected beam 102 to the detector 110 be nominally equal to the optical path length of the transmitted beam 103 to the near THz or THz transmitter 111.

The near THz or THz transmitter 111 includes a transmit antenna operable for emitting THz or near THz radiation pulses having a frequency between 0.05 THz and 50 THz at a sample location on the sheet material. The THz transmission antenna will generally have a bias voltage applied to it (not shown in FIG. 5), which can be modulated be used for the utilization of a lock-in detection scheme in system 100. The detector 110 includes a receive antenna operable to receive near THz or THz radiation transmitted by the location on the sample 130 that is irradiated by the incident radiation. Embodiments of the invention are not limited to using photoconductive antennae as described herein. For example, other methods such as optical rectification using crystals such as Zinc Telluride (ZnTe) may also be used. The THz detector 110 is coupled to the receive antenna and is also coupled to receive the delayed optical pulses from delay comprising optics 108 for synchronously detecting the THz or near THz radiation transmitted by the sheet material sample 130. The detector 110 generates electrical detection signals. Although FIG. 1 shows a THz focused beam interacting with the sample 130, it is that other optical geometries such as a collimated geometry can also be used.

A signal processing system 125 is coupled to the detector 110 to receive the electrical detection signals. The signal processing system 125 comprises a memory 126 for storing calibration data that is generally in the form of calibration coefficients that permit calculation of the moisture content, caliper or basis weight of the sheet material. Memory 126 can also include a stored estimate for the refractive index for a dry sample of the sheet material and the density of the sheets dry content. Signal processing system 125 also includes processing electronics 128 that generally includes a transimpedance (current to voltage)-amplifier, filter and analog to digital (A/D) converter. A processor (e.g. DSP) 127 receives processed electrical signal (amplified, filtered and converted to a digital signal) from processing electronics 128. The processor 127 combines a signal associated with the transmitted pulse together with the calibration data and a reference signal pulse to determine at least one property of the sheet material sample selected from the moisture content, basis weight and caliper.

With respect the reference pulses and to techniques for applying the correction, processor 127 in signal processing system 125 (FIG. 5) can compare the continuous set of reference pulses with sample pulses and execute the necessary corrections for time jitter and amplitude variations.

The detection electronics generally utilizes a lockin detection scheme (not shown in FIG. 5) in which a modulated bias voltage is applied to the transmitter antenna. This modulation signal is also fed to lock-in detection electronics that increases the signal-to-noise ratio of the system as well as minimizes the effect of any background signal. A mechanical chopper can be used in the source femtosecond laser beam 105 to realize the lock-in detection—in the case a DC bias voltage is applied to the antenna.

Figure 6:
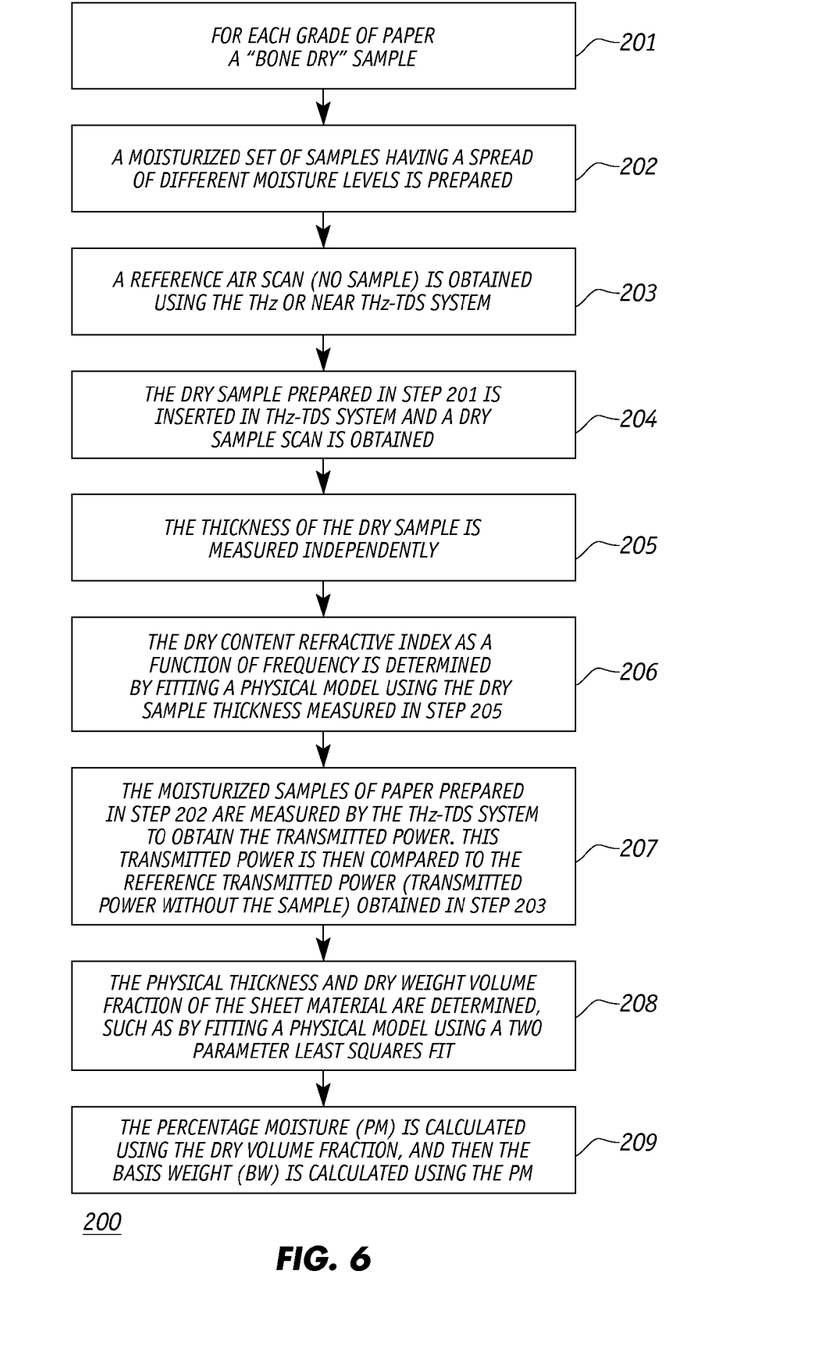
FIG. 6 shows an exemplary method for obtaining caliper (thickness), basis weight and percent moisture for a sheet material sample described as being paper, from a THz or near THz-TDS system, such as the transmission system shown in FIG. 5.

An exemplary method 200 is described below for coincidentally obtaining caliper (thickness), basis weight and percent moisture for a sheet material sample described as being paper, from a THz or near THz-TDS system, such as system 100. Referring to FIG. 6, in step 201, for each grade of paper a "bone dry" sample (essentially moisture free, hereafter a "dry sample") is made following standard procedures known in the art. In step 202, for each grade of paper, a moisturized set of samples having a spread of different known moisture levels is prepared. These samples should cover the moisture range over which the system generally operates. Step 203 comprises a reference air scan (i.e. a scan with no sample present) using the THz or near THz-TDS system. In step 204 the dry sample prepared in step 201 is inserted in THz-TDS system and a dry sample scan is obtained. In step 205 the thickness of the dry sample is measured independently. One method for measuring the thickness of the dry sample is a lab TAPPI gauge.

In step 206 the dry content refractive index as a function of frequency is determined by fitting a physical model using the dry sample thickness measured in step 205. The dry content refractive index of the sample can then be calculated by fitting the model for the transmittance function for a transmittance-based system (equation (1)) or the reflectance function for a reflection-based system (equation (7)). When the fit is performed the thickness measurement from step 205 (e.g. from the TAPPI caliper gauge) is input and it is generally assumed that the contribution of water to the dry refractive index of the sample is negligible, i.e. we the dry content fraction to 1. From this fit the dry content refractive index is obtained which generally constitutes one of the calibration parameters. For paper this dry content refractive index parameter typical lies between 1.3 and 1.5 in the THz region.

The physical model for step 206 can comprise modeling the sheet material (e.g. paper) as a thin dielectric slab comprising a mixture of air, dry content (cellulose and ash), and water. The Bruggeman model was employed where the proportions of the mixture and the thickness of the sheet material can be varied. Existing data for the dielectric constant of water in the THz regime at different temperatures can be obtained. A double Debye model can be used to model the electromagnetic response of the water at the near THz or THz frequency.

For example, the model fitting for step 206 can comprise performing a least squares fit. It can be assumed that the sample consists entirely of the dry sample (i.e., 0% moisture).

Figure 7:
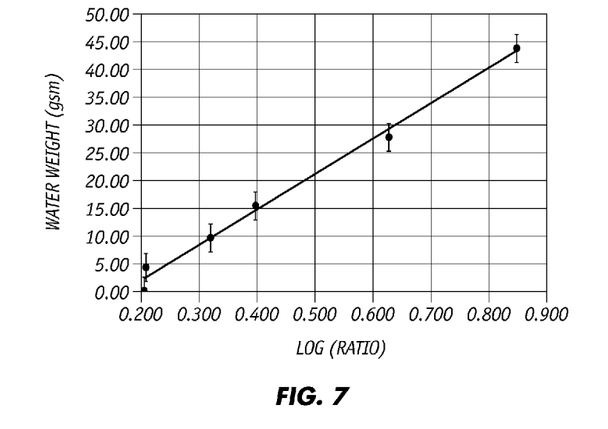
FIG. 7 is a calibration curve that relates the water weight (WW) to the log of the ratio the integrated power spectral density of a reference transmitted pulse and a measured transmitted pulse.

Step 207 comprises measuring the moisturized samples of paper prepared in step 202 using the THz-TDS system to obtain the transmitted power or the transmitted field in the case of a transmission-based system, or reflected power or reflected field in the case of a reflectance-based system. In the case of a transmission-based system, the transmitted power or transmitted field is then compared to the reference transmitted power (transmitted power without the sample) obtained in step 203. The calibration curve for WW can be displayed as shown in FIG. 7. The following function is plotted in FIG. 7:

$$WW(y_i(t), y_o(t)) = m \times \log_e\left(\frac{PSD(y_i(t))}{PSD(y_o(t))}\right) + C \tag{8}$$

Where WW is the water weight in grams per square meter (GSM), $y_i(t)$ is the reference or incident pulse (no sample present), $y_o(t)$ is the output or sample pulse (sample present) and m and C are calibration constants. PSD stands for the integrated power spectral density and is defined as the integral over frequency of the norm-squared Fourier transform. WW shown in FIG. 7 plotted against the log of the ratio of the reference and sample pulse power can be seen to be essentially linear, although there is no requirement for a linear function.

Figure 8:
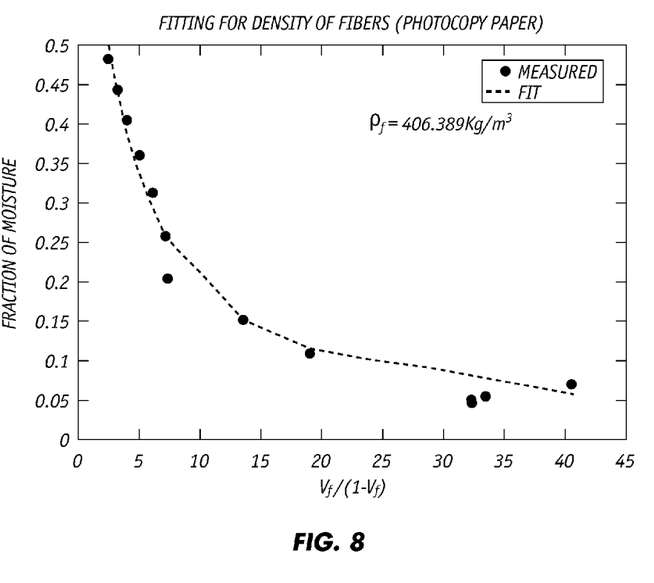
FIG. 8 shows a calibration curve fit based on measured values for the fraction of moisture obtained from photocopy paper.

The same data set obtained from the moisturized sample set in step 202 can be used to obtain another calibration parameter, density of dry content, $\rho_f$. This calibration parameter can be obtain by constructing a plot of fractional moisture content versus $(v_f/(1-v_f))$ and fitting the expression given in equation (9) to obtain $\rho_f$. This fit is shown in FIG. 8, which shows a calibration curve fit based on measured values faction of moisture values obtained from a sample comprising photocopy paper. The abscissa in this figure is $v_f/(1-v_f)$ where $v_f$ is the dry weight volume fraction obtained from the fit of the physical to the transmitted THz pulse. The ordinate in FIG. 8 is the fractional water content for the sample under test. This fractional water content can be obtained using an independently measurement technique and typically be obtained gravimetrically in a laboratory. The density of dry paper content can be obtained by a least squares parameter fit to the model:

$$PM = \frac{\rho_f}{\rho_w}\left(\frac{1}{v_f} - 1\right) \tag{9}$$

Where PM is the percent moisture and $\rho_w$ and $\rho_f$ are the densities of water and dry paper content. The density of water can be obtained from open literature.

Figure 9:
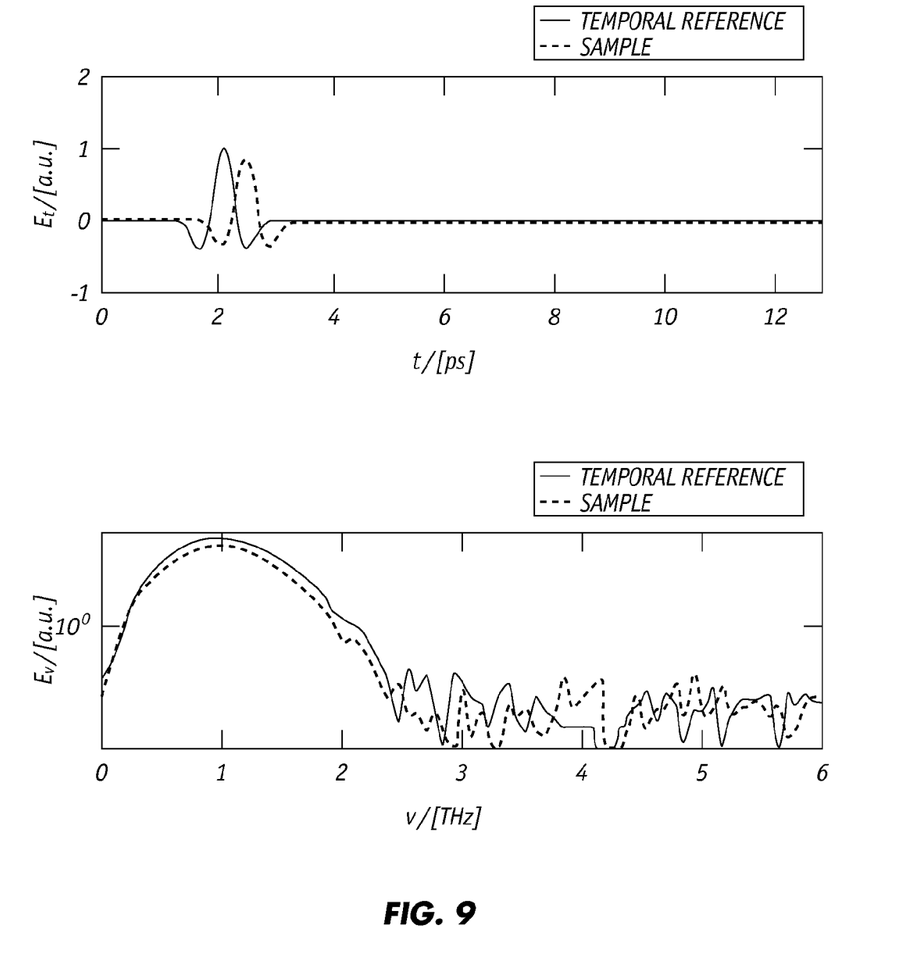
FIG. 9 shows typical simulated input and output temporal pulses from a transmission-based TEL or near THz-TDS system. The top traces show the temporal trace (time in picoseconds) for the electric field for the temporal reference and sample pulses obtained from the THz-TDS system and the bottom traces are their Fourier transform.

Typical input and output temporal pulses from the THz-TDS that were simulated are shown in FIG. 9. The top traces show the temporal trace (time in picoseconds) for the electric field for the temporal reference and sample pulses obtained from the THz-TDS system and the bottom traces are their Fourier transforms (frequency in THz).

Figure 10:
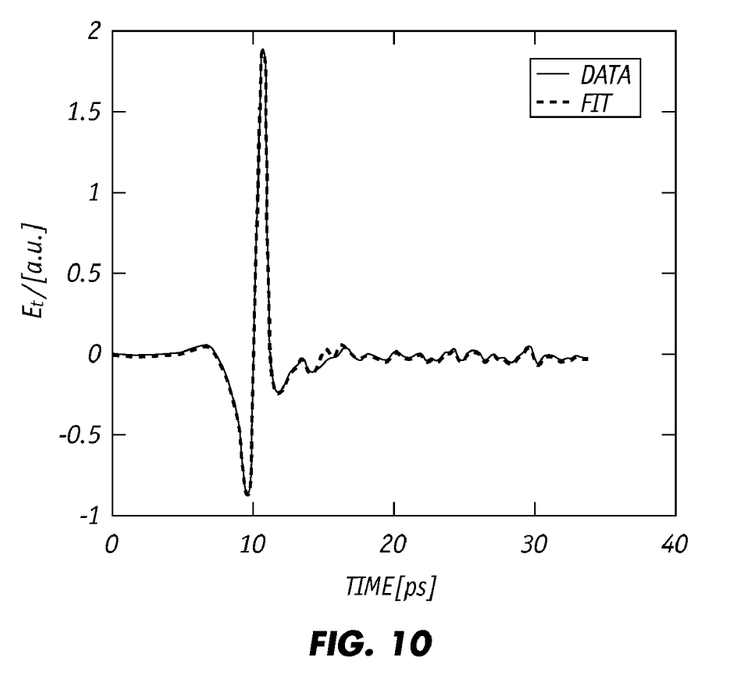
FIG. 10 shows a physical model fitted to the signal data obtained by transmission of a THz pulse through paper.

In step 208, in the case of a transmittance system, in order to obtain the physical thickness and dry weight volume fraction of the sheet material sample a transmittance function for the sheet material can be used (see equation (1) provided above). The parameters in the transmittance function can be adjusted to minimize the least squares error between the calculated transmission pulse and the measured transmitted pulse, thus fitting the physical model using a two parameter least squares fit. FIG. 10 shows a physical model fitted to the signal data obtained by transmission of a THz pulse through paper. The calculated transmission pulse can be found using the convolution (in time domain) of the reference pulse with the transmittance function. Defining, $$y_o^{calc}[k] = IFFT(\{Y_i[\omega] \cdot T(\omega, h, v_f)\})$$

The error function can be defined as:

$$\text{Error} = \sum_k |y_o^{meas}[k] - y_o^{calc}[k]|^2 \tag{10}$$

h: Physical Thickness $v_f$: Dry weight volume fraction

Minimizing the error function above can provide the physical thickness (h) and dry weight volume fraction, $v_f$ of the paper or other sheet material. In step 209, the PM and then the BW can be calculated as follows:

$$PM = \frac{\rho_f}{\rho_w}\left(\frac{1}{v_f} - 1\right) \tag{11}$$

$$BW = \frac{WW}{PM}, \tag{12}$$

where:

$\rho_f$: Fiber density $\rho_w$: Water density

Figure 11:
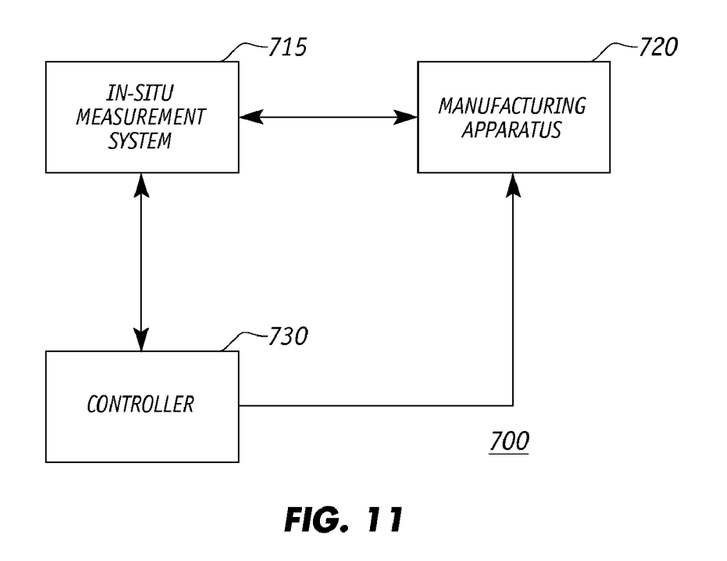
FIG. 11 is block diagram of an exemplary close loop controlled sheet material manufacturing system that provides in-situ measurements during the papermaking process. The system includes a process controller that uses the in-situ measurements for controlling process variables to maintain output quality and minimize the quantity of rejected product.

FIG. 11 is block diagram of an exemplary close loop controlled sheet material manufacturing system 700 that provides in-situ coincident measurements of a plurality of properties of a sheet material during the sheet material (e.g. paper) making process. The closed loop control provided as described below helps control process variables to maintain output quality and minimize the quantity of rejected product. The system 700 comprises a sheet material manufacturing apparatus 720 and a process controller 730 that uses the in-situ measurements from an in-situ measurement system 715. Measurement system 715 can be a reflection-based system, or a transmission based system such as system 100 shown in FIG. 1. Although shown as wire connected, communications between the components of system 700 can be wired, optical (e.g. fiber optic), or over the air (e.g. RF) or combinations thereof.

The controller 730 can process the electrical detection signals received and determine one or more paper quality properties, for example, the moisture profile achieved, and how the moisture profile should be updated during the paper-making process from "wet-end"-to-press and press-to-dryers at the "dry-end" in the case of a paper making system. As known in the art, the moisture profile can have significant impact on known variables in the paper making process such as sheet tension profiles, sheet breaks, shrinkage, winder efficiency, pressroom operation.

The foregoing has described the principles, preferred embodiments and modes of operation of the present invention. However, the invention should not be construed as being limited to the particular embodiments discussed. Thus, the above-described embodiments should be regarded as illustrative rather than restrictive, and it should be appreciated that variations may be made in those embodiments by workers skilled in the art without departing from the scope of the present invention as defined by the following claims.

What is claimed is:

1. An apparatus that has a continuous reference for measuring at least one property of a sample that comprises:
    a radiation source that generates pulses of radiation;
    means for splitting the pulses of radiation to yield reference radiation pulses and sample radiation pulses wherein the sample radiation pulses are directed to the sample; and
    a detector positioned for receiving the reference radiation pulses wherein the reference radiation pulses do not interact with the sample, and wherein the detector is positioned for receiving the sample radiation pulses that emerge from the sample wherein the reference and sample pulses from the means for splitting the pulses of radiation are separated in time so that the reference pulses reach the detector at different times relative to the sample pulses.

2. The apparatus of claim 1 further comprising a first mirror that is positioned to reflect sample radiation pulses that are reflected from the sample.

3. The apparatus of claim 2 further comprising a second mirror that is positioned to reflect the reference radiation pulses to a single detector.

4. The apparatus of claim 1 further comprising a first mirror that is positioned to reflect sample radiation pulses that are transmitted through the sample.

5. The apparatus of claim 1 wherein the reference and sample pulses are measured using a single detector.

6. The apparatus of claim 1 comprising:
    a laser source that generates pulses of radiation; and
    means for splitting the pulses of radiation from the laser source to yield first radiation pulses and second radiation pulses;
    wherein the radiation source comprises an emitter that generates terahertz frequency signal pulses when excited by the first radiation pulses from the laser source and wherein the detector receives terahertz frequency radiation that emerges from the sample and that generates detection signals when excited by the second radiation pulses.

7. An apparatus that has a continuous reference for measuring at least one property of a sample that comprises:
    a radiation source that generates pulses of radiation;
    means for splitting the pulses of radiation to yield reference radiation pulses and sample radiation pulses wherein the sample radiation pulses are directed to the sample;
    a detector positioned for receiving the reference radiation pulses wherein the reference radiation pulses do not interact with the sample, and wherein the detector is positioned for receiving the sample radiation pulses that emerge from the sample; and
    means for correcting time jitter based on detection of the reference radiation pulses.

8. An apparatus that has a continuous reference for measuring at least one property of a sample that comprises:
    a radiation source that generates pulses of radiation;
    means for splitting the pulses of radiation to yield reference radiation pulses and sample radiation pulses wherein the sample radiation pulses are directed to the sample;
    a detector positioned for receiving the reference radiation pulses wherein the reference radiation pulses do not interact with the sample, and wherein the detector is positioned for receiving the sample radiation pulses that emerge from the sample; and
    means for correcting amplitude variations based on detection of the reference radiation pulses.

9. A time-domain spectroscopy apparatus that has a continuous reference for measuring at least one property of a sample that comprises:
    an emitter that generates pulses of radiation;
    means for splitting the pulses of radiation to yield reference radiation pulses and sample radiation pulses wherein the sample radiation is directed to the sample and wherein the reference radiation pulses do not interact with the sample;
    a first mirror positioned to reflect sample radiation that has been transmitted through or reflected from the sample;
    a second mirror positioned to reflect the reference radiation pulses; and
    a detector positioned for receiving the reflected reference radiation pulses and the reflected sample radiation pulses wherein the means for splitting the pulses of radiation comprises a beam splitter and wherein the reference and sample pulses from the beam splitter are separated in time so that the reference pulses reach the detector at different times relative to the sample pulses.

10. The time-domain spectroscopy apparatus of claim 9 wherein the reference and sample pulses are measured using a single detector.

11. The time-domain spectroscopy apparatus of claim 9 wherein the first mirror is positioned to reflect sample radiation that has been transmitted through the sample.

12. A time-domain spectroscopy apparatus that has a continuous reference for measuring at least one property of a sample that comprises:
    an emitter that generates pulses of radiation;
    means for splitting the pulses of radiation to yield reference radiation pulses and sample radiation pulses wherein the sample radiation is directed to the sample and wherein the reference radiation pulses do not interact with the sample;
    a first mirror positioned to reflect sample radiation that has been transmitted through or reflected from the sample;

a second mirror positioned to reflect the reference radiation pulses;

a detector positioned for receiving the reflected reference radiation pulses and the reflected sample radiation pulses: and means for correcting time jitter based on detection of the reference radiation pulses.

13. A time domain spectroscopy apparatus that has a continuous reference for measuring at least one property of a sample that comprises:

an emitter that generates pulses of radiation;

means for splitting the pulses of radiation to yield reference radiation pulses and sample radiation pulses wherein the sample radiation is directed to the sample and wherein the reference radiation pulses do not interact with the sample;

a first mirror positioned to reflect sample radiation that has been transmitted through or reflected from the sample;

a second mirror positioned to reflect the reference radiation pulses:

a detector positioned for receiving the reflected reference radiation pulses and the reflected sample radiation pulses; and means for correcting amplitude variations based on detection of the reference radiation pulses.

14. A method of improving the precision of a time-domain spectroscopy apparatus that includes an emitter that generates pulses of radiation and a detector that receives pulses of radiation that emerge from a sample, the method comprising the steps of:

positioning a beam splitter along an optical path between the emitter and the detector to form reference radiation pulses and sample radiation pulses that are directed to the sample and the reference radiation pulses do not interact with the sample;

positioning a first mirror to reflect sample radiation pulses to the detector, and positioning a second mirror to reflect reference radiation pulses to the detector and using the reflected radiation pulses to monitor fluctuations in phase and amplitude of the reference radiation pulses wherein the reference and sample pulses from the beam splitter are separated in time so that the reference pulses reach the detector at different times relative to the sample pulses.

15. The method of claim 14 wherein the reference and sample pulses are measured using a single detector.

16. A method of improving the precision of a time-domain spectroscopy apparatus that includes an emitter that generates pulses of radiation and a detector that receives pulses of radiation that emerge from a sample, the method comprising the steps of:

positioning a beam splitter along an optical path between the emitter and the detector to form reference radiation pulses and sample radiation pulses that are directed to the sample and the reference radiation pulses do not interact with the sample:

positioning a first mirror to reflect sample radiation pulses to the detector;

positioning a second mirror to reflect reference radiation pulses to the detector and using the reflected radiation pulses to monitor fluctuations in phase and amplitude of the reference radiation pulses; and correcting time jitter based on detection of the reference radiation pulses.

17. A method of improving, the precision of a time-domain spectroscopy apparatus that includes an emitter that generates pulses of radiation and a detector that receives pulses of radiation that emerge from a sample, the method comprising the steps of:

positioning a beam splitter along an optical path between the emitter and the detector to form reference radiation pulses and sample radiation pulses that are directed to the sample and the reference radiation pulses do not interact with the sample;

positioning a first mirror to reflect sample radiation pulses to the detector;

positioning a second mirror to reflect reference radiation pulses to the detector and using the reflected radiation pulses to monitor fluctuations in phase and amplitude of the reference radiation pulses; and correcting amplitude variations based on detection of the reference radiation pulses.

\* \* \* \* \*